United States Patent [19]

Jacobson et al.

[11] Patent Number: 4,496,781

[45] Date of Patent: Jan. 29, 1985

[54] PROCESS FOR THE PRODUCTION OF ETHYLENE GLYCOL THROUGH THE HYDROFORMYLATION OF GLYCOL ALDEHYDE

[75] Inventors: Stephen E. Jacobson, Morristown, N.J.; Chun F. Chueh, Jamaica, N.Y.

[73] Assignee: The Halcon SD Group, Inc., New York, N.Y.

[21] Appl. No.: 597,003

[22] Filed: Apr. 5, 1984

[51] Int. Cl.³ .................... C07C 31/20; C07C 29/14
[52] U.S. Cl. ................................. 568/862; 568/462
[58] Field of Search ............................ 568/862, 462

[56] References Cited

U.S. PATENT DOCUMENTS

| 4,079,085 | 3/1978 | Wall | 568/862 |
| 4,144,401 | 3/1979 | Wall | 568/862 |
| 4,200,765 | 4/1980 | Goetz | 568/862 |
| 4,382,148 | 5/1983 | Drent | 568/462 |
| 4,405,814 | 9/1983 | Carroll et al. | 568/462 |
| 4,405,821 | 9/1983 | Goetz | 568/862 |

Primary Examiner—J. E. Evans
Attorney, Agent, or Firm—William C. Long; Riggs T. Stewart; Daniel R. Zirker

[57] ABSTRACT

A process for the preparation and purification of a glycol aldehyde intermediate which is later hydrogenated to ethylene glycol is disclosed. The process proceeds via the catalytic reaction of formaldehyde, carbon monoxide and hydrogen and utilizes a novel class of lipophilic rhodium phosphine amide catalysts and an effective solvent mixture, which enables efficient catalyst separation and recycle without the loss of a substantial amount of the expensive catalyst.

26 Claims, 1 Drawing Figure

PROCESS FOR THE PRODUCTION OF ETHYLENE GLYCOL THROUGH THE HYDROFORMYLATION OF GLYCOL ALDEHYDE

BACKGROUND OF THE INVENTION

1. Field of the Invention

This invention is related to a process for the preparation of glycol aldehyde, and more particularly, is related to the preparation and purification of glycol aldehyde which is subsequently hydrogenated to ethylene glycol; the process proceeding via the catalytic reaction of formaldehyde, carbon monoxide and hydrogen and utilizing a novel class of lipophilic rhodium-phosphine-amide catalysts and an effective solvent mixture. The process features high reactant conversions, selectivities, product and recyclable catalyst recoveries.

2. Description of the Prior Art

Glycol aldehyde is well known as a valuable intermediate in a variety of organic reactions, and is particularly useful as an intermediate in the production of ethylene glycol.

Ethylene glycol is well known as a valuable industrial chemical having a wide variety of uses, such as a coolant, an anti-freeze, a monomer for polyester production, and an industrial solvent.

The reaction of formaldehyde with carbon monoxide and hydrogen at elevated temperatures and superatmospheric pressures in the presence of a variety of catalysts is a well known reaction and yields glycol aldehyde, as well as methanol and lesser amounts of polyhydroxy compounds, which must be separated from the glycol aldehyde. U.S. Pat. No. 3,920,753 discloses the production of glycol aldehyde from the reaction of formaldehyde, carbon monoxide and hydrogen in the presence of a cobalt catalyst under controlled reaction conditions, however, the process produces relatively low yields of product. Japanese Pat. No. J57-118,527 describes the production of glycol aldehyde by using a ruthenium catalyst system. European Patent Application No. 002,908 describes a process for the production of glycol aldehyde from the reaction of formaldehyde, in the presence of a rhodium-triphenyl-phosphine ligand catalyst, with carbon monoxide and hydrogen, in a tertiary amide solvent. This reference further suggests that the glycol aldehyde product is preferably extracted from a water-immiscible hydroformylation solvent. However, the proposed method suffers from the drawback of limiting the choice of hydroformylation solvent to the class of water immiscible solvents, whereas the most effective hydroformylation solvents, such as acetonitrile, are very water soluble. Furthermore, when extracting glycol aldehyde with an aqueous extractant, even when using a water-immiscible solvent, a substantial amount of the expensive rhodium catalyst migrates into the water phase and is lost, thereby decreasing both the amount and the resultant activity of the remaining catalyst.

U.S. Pat. No. 4,291,179 describes a similar reaction for the production of acetaldehyde in which trifluoroacetic acid is added to produce ethylene glycol. U.S. Pat. No. 4,356,332 describes the preparation of ethylene glycol from the reaction of synthesis gas and formaldehyde, using a rhodium or cobalt catalyst in the presence of a substantially inert oxygenated hydrocarbon solvent. European Patent Application No. 82/200,272.1 describes a process for the preparation of glycol aldehyde which comprises reacting formaldehyde, hydrogen and carbon monoxide in the presence of either a rhodium or cobalt containing catalyst precursor, together with a strong protonic acid, a tertiary amide solvent and a triaryl phosphine. U.S. Pat. No. 4,200,765 discloses a process of preparing glycol aldehyde involving reacting formaldehyde, carbon monoxide, and hydrogen in a tertiary amide solvent in the presence of a catalytic amount of rhodium in complex combination with carbon monoxide, using triphenylphosphine as the preferred catalyst promoter. U.S. Pat. No. 4,405,814 discloses a similar process for the production of glycol aldehyde, incorporating a tertiary organo phosphorous or arsenic moiety into the rhodium catalyst together with a basic organo amine. U.S. Pat. No. 4,405,821 discloses still another similar process involving carrying out the reaction in the presence of a glycol aldehyde yield enhancing phosphine oxide.

A major flaw in the prior art processes utilizing transition metal-phosphine catalysts has been the inability to recover a satisfactory amount of the expensive metal, e.g., rhodium, catalyst after the hydroformylation reaction, thus frustrating the desire to recycle and reuse the catalyst. In the propylene hydroformylation of n-butyraldehyde large excesses of triarylphosphine (U.S. Pat. No. 4,277,627) coupled with the introduction of small quantities of diarylalkylphosphine (U.S. Pat. No. 4,260,828) were used to stabilize the resulting rhodium compounds. However, in the instant formaldehyde hydroformylation process such an excess of either alkyl or arylphosphine is not feasible, due to the resulting substantial increase in methanol selectivity at the expense of glycol aldehyde selectivity when operating with an increased phosphine concentration, i.e., above a three to one phosphine to rhodium ratio.

The prior art processes for the production of glycol aldehyde have also produced a wide mixture of undesired reaction products, such as polymeric formaldehyde and methanol. Consequently, time-consuming separation procedures are required, a fact that the patent literature tends to gloss over, as well as a corresponding reduction in the amount of desired product formed. Additional problems involved in the hydroformylation of formaldehyde to glycol aldehyde are the rapid decline in activity of the transition metal catalyst, the presence of competing aldol condensation and acetal formation reactions hampering the separation of the product, and the formation of catalyst-poisoning amines.

In copending U.S. Patent Application Ser. No. 508,704, filed June 28, 1983, several of these problems were solved by the utilization of a novel class of phosphine-amide catalysts having the formula: $MX_x(CO)_y[P(R_1)_2R_2C(O)—NR_3R_4]_z$, wherein M is an element selected from the group of rhodium, cobalt, and ruthenium, preferably rhodium; X is an anion, preferably a halide, a pseudohalide, a hydride or a deprotonated strong carboxylic acid; P is phosphorous; $R_1$ is an aromatic or aliphatic group of 1-20 carbon atoms, preferably aromatic; $R_2$ is an organo group containing from 0 to 20 carbon atoms of either aliphatic or aromatic nature and may also include oxygen, nitrogen or sulfur atoms, which atoms may be directly bonded to the amide C(O)N carbon, or nitrogen; $R_3$ and $R_4$ are each aliphatic or aromatic groups containing from 1 to 50 carbon atoms; the resultant compound being characterized by the absence of hydrogen on the amide nitrogen atom and the additional limitation that if $R_2$ is bonded to the amide nitrogen, then either $R_3$ or $R_4$ is bonded to the amide carbon; x ranges from 0 to 3, y ranges from 1 to 5, and z from 1 to 4. However, the most preferred rhodium-phosphine-amide catalysts cited in this formaldehyde hydroformylation system are ineffective as catalysts for the subsequent glycol aldehyde hydrogenation to ethylene glycol. Consequently, it becomes essential for commercial success to be able to extract the glycol aldehyde from the reaction mixture and either subsequently hydrogenate it to ethylene glycol in the presence of an effective catalyst, or utilize it in another manner. However, we have discovered that the phosphine-amide catalysts have a strong tendency to migrate into the glycol aldehyde product phase and cannot be readily recovered, thereby ruining the economics of the resulting process, which requires an active recyclable catalyst.

Thus, it is an object of this invention to provide an improved process for the hydroformylation of glycol aldehyde and its subsequent hydrogenation to ethylene glycol which has high conversions and selectivities, from the reaction of formaldehyde, carbon monoxide and hydrogen feedstocks.

It is another object of this invention to provide a process wherein the glycol aldehyde and the transition metal-phosphine-amide catalyst can be easily separated and extracted or recycled from the reaction product mixture in an effective industrial operation.

It is still another object of this invention to develop a process wherein the hydroformylation catalyst is substantially prevented from migrating into the glycol aldehyde product phase during separation, thus preventing the loss of the expensive catalyst.

It is still another object of this invention to provide a process for the hydroformylation of formaldehyde which is able to recycle the rhodium catalyst a substantial number of times without suffering a substantial loss in catalyst activity.

SUMMARY OF THE INVENTION

Accordingly, the invention provides for an improved process for the preparation of glycol aldehyde from the hydroformylation of formaldehyde and the subsequent hydrogenation of glycol aldehyde to ethylene glycol, comprising reacting formaldehyde, hydrogen and carbon monoxide in a suitable hydroformylation reaction zone in the presence of an effective solvent mixture comprising a relatively low boiling, polar, organic, hydroformylation solvent, e.g., acetonitrile, a relatively high boiling, non-polar, organic, solvent, e.g., xylene, and a low boiling organic separation enhancing solvent; e.g., diethyl ether, the most preferred mixture being an acetonitrile-xylene-diethyl ether mixture; under suitable superatmospheric pressure and elevated temperature conditions, and in the further presence of at least one member of a class of catalytic lipophilic phosphine-amide ligands, i.e., most preferably $PPh_2CH_2CH_2C(O)N(CH_3)[(CH_2)_{17}CH_3]$ (Ph represents phenyl) in conjunction with an effective transition metal, preferably rhodium. The hydroformylation zone effluent is passed to a first distillation zone, where the hydroformylation solvent, together with any formed methanol and separation enhancing solvent, are distilled from the remainder of the reaction mixture, now comprising the high boiling non-polar solvent, glycol aldehyde, unreacted polymeric formaldehyde, and the lipophilic rhodium-phosphine-amide catalyst, which is stabilized in the presence of a CO-rich, low temperature, low pressure environment. In the preferred case acetonitrile, methanol and diethyl ether are taken off and passed to a second distillation zone, wherein the ether and methanol are separated therefrom and passed to and separated in a third distillation zone; the acetonitrile preferably being partially recycled to the hydroformylation zone for reuse in the process.

The stream comprising the distillation bottoms, or remaining hydroformylation zone mixture is passed from the first distillation zone to a separation zone, wherein the glycol aldehyde and unreacted formaldehyde are separated into a phase, i.e., precipitated, from the mixture, collected and passed to an extraction zone wherein the precipitates are contacted and washed with the separation enhancing solvent stream, preferably diethyl ether passed from the third distillation zone. The ether extracts the remaining high boiling, non-polar solvent, e.g., xylene still present in the glycol aldehyde-formaldehyde phase together with the remaining catalyst, allowing at most about 100 ppm of catalyst to be lost, and passes the glycol aldehyde-formaldehyde phase to a fourth distillation zone, wherein a suitable amount of preferably, recycled low boiling polar organic, e.g., acetonitrile from the second distillation zone, contacts the phase and breaks up the formaldehyde polymer in a high temperature, low pressure distillation. An acetonitrile-formaldehyde stream is distilled and preferably recycled to the hydroformylation reaction zone, while the remaining bottoms stream comprising glycol aldehyde and the remainder of the acetonitrile is passed to a stripping zone, in which acetonitrile is stripped off by contacting with a carbon monoxide gas stream. The resulting acetonitrile-CO mixture is preferably recycled to the hydroformylation zone, while the separated glycol aldehyde is dissolved in a suitable polar organic solvent, e.g., ethylene glycol, and the resulting solution passed to a hydrogenation zone where it is hydrogenated to ethylene glycol and subsequently separated from any remaining by-products, purified and taken off as product.

The hydroformylation catalyst during precipitation of and contacting with the glycol aldehyde in the separation zone remains substantially in the xylene cosolvent without migrating into the glycol aldehyde phase, and is recycled to the hydroformylation zone, as is the ether stream, which as described above, contacts and washes the residual xylene-catalyst containing particles present on the glycol aldehyde. The recycled solvents and catalyst streams are preferably recharged with fresh feed, and the process is continued.

DETAILED DESCRIPTION OF THE INVENTION

Figure 1:
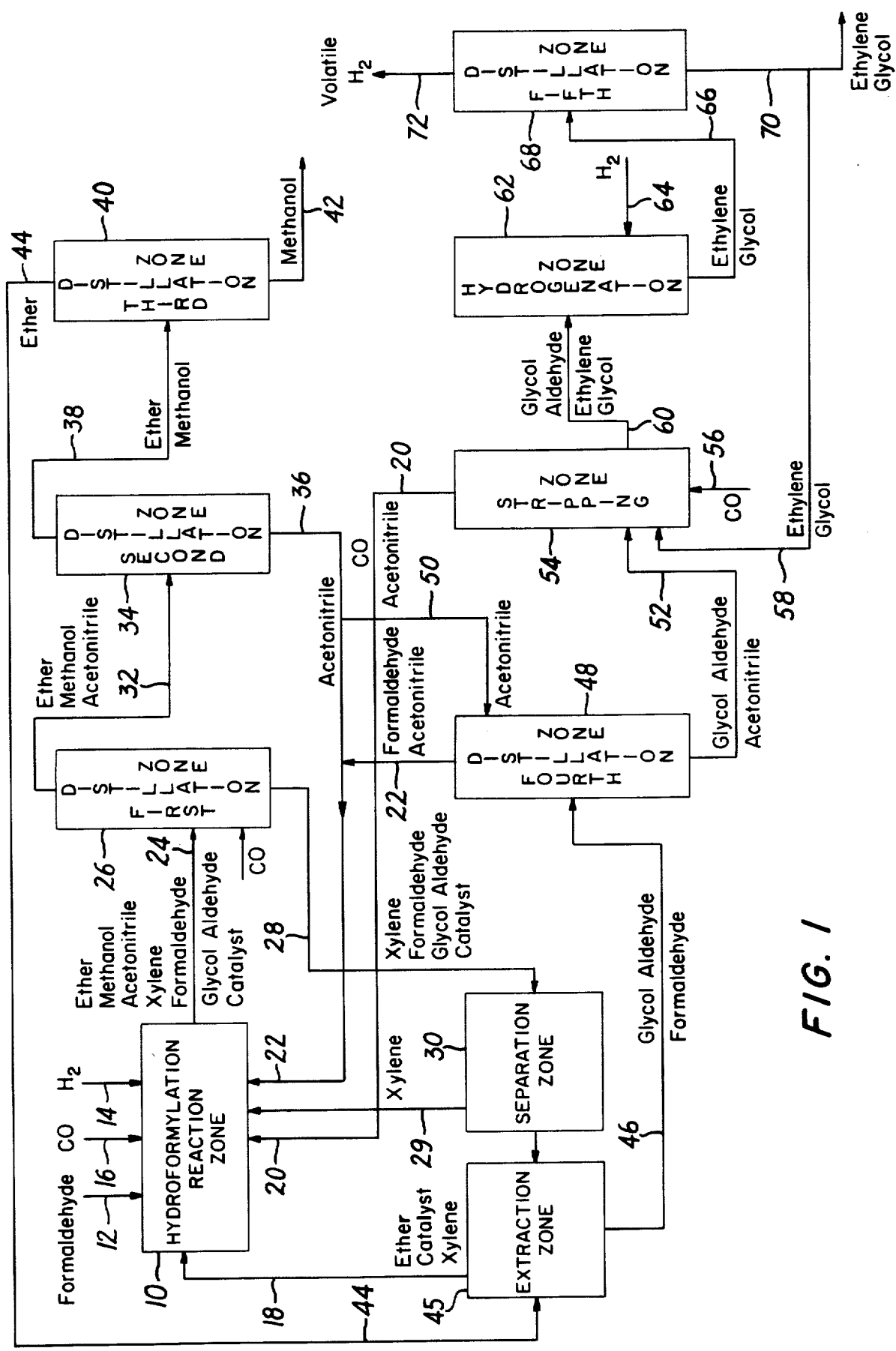

The invention, in the broadest embodiment, comprises a process for the preparation of ethylene glycol through a glycol aldehyde intermediate comprising:

(A) reacting formaldehyde, hydrogen and carbon monoxide in hydroformylation reaction zone to form glycol aldehyde in the presence of an effective solvent mixture comprising:
(1) a low boiling, polar, organic, hydroformylation solvent,
(2) a high boiling, non-polar organic solvent,
(3) a low boiling organic separation enhancing solvent;
the reaction proceeding in the presence of a lipophilic catalyst selected from a class of phosphine-amide ligands in conjunction with an effective transition metal;

(B) separating the hydroformylation solvent and the separation enhancing solvent from the hydroformylation zone effluent;

(C) separating the glycol aldehyde-unreacted formaldehyde phase from the remaining reaction zone effluent, now comprising the high boiling, non-polar organic solvent containing the lipophilic catalyst.

(D) contacting and washing the separated glycol aldehyde-formaldehyde phase with the separation enhancing solvent in an extraction zone to substantially extract the remaining high boiling, non-polar organic as well as any catalyst contained therein.

(E) recycling the separation enhancing solvent and the high boiling, non-polar organic solvent containing substantially all the lipophilic catalyst to the hydroformylation zone;

(F) separating the glycol aldehyde from the formaldehyde;

(G) hydrogenating the glycol aldehyde in a hydrogenation zone to ethylene glycol;

(H) separating ethylene glycol from the hydrogenation zone effluent.

The process of the present invention is accomplished by first reacting formaldehyde, carbon monoxide and hydrogen feed streams in the presence of a mixture of at least one low boiling, e.g., below about 90° C., at atmospheric pressure, polar organic hydroformylation solvent, most preferably acetonitrile, at least one higher boiling, e.g., above about 100° C., at atmospheric pressure, organic, non-polar solvent, most preferably xylene, and in the further presence of at least one low boiling, organic separation enhancing solvent, e.g., diethyl ether and the like, the solvent preferably having a substantial density difference from the glycol aldehyde-formaldehyde mixture and being substantially immiscible to glycol aldehyde, as well as being capable of dissolving the non-polar solvent and the catalyst. Additionally, such a solvent should also be capable of breaking any azeotrope formed by methanol and the hydroformylation solvent. The reaction takes place in the presence of a hydroformylation catalyst selected from a class of lipophilic transition metal-phosphine-amide ligands, at elevated temperatures and superatmospheric pressures, that is, under conditions suitable for effective hydroformylation. A variety of solvents are suitable for use in the process, but it is essential that the boiling point difference between the relatively low boiling, organic polar hyroformylation enhancing solvent and the relatively high boiling organic non-polar solvent is at least sufficient to enable effective separation, e.g., about 10° C., so that an effective separation through distillation can take place. Most preferably, the process is accomplished by incorporating at least one member of a preferred class of catalytic lipophilic rhodium-phosphine-amides disclosed in copending U.S. patent application Ser. No. 596,994, filed concurrently herewith, the disclosure of which is incorporated by reference, into the process cycle.

The process of this invention will be more readily understood by reference to the accompanying diagram which discloses, solely for purposes of simple explanation, the process for carrying out the preferred embodiment using the preferred reactants and solvents of this invention. Thus, referring to the drawing, the reference numeral 10 represents a hydroformylation reaction zone, which may comprise one or more reactors of any particular type known to those skilled in the art, and into which are passed formaldehyde, hydrogen and carbon monoxide feed streams 12, 14 and 16 together with, preferably, four recycle/feed streams 18, 20, 22 and 29, stream 18 containing primarily diethyl ether, as well as minor amounts of xylene and the lipophilic hydroformylation catalyst, stream 22 comprising acetonitrile and formaldehyde, stream 20 comprising acetonitrile and carbon monoxide, and stream 29 comprising xylene. Any of these streams as well as reaction zone 10 can be recharged with fresh catalyst or various solvent component streams (not shown). The exact manner of contacting the reactant, solvent and catalyst streams in the reactor is not critical, as any of the procedures known in the art for hydroformylation reactions can be used so long as there is suitable efficient gas and liquid contact. Thus, for example, the process may be carried out by contacting a solution of formaldehyde together with the preferred catalyst, organic solvent mixture and a mixture of carbon monoxide and hydrogen at the selected reaction conditions. Alternatively, the solution of formaldehyde may be passed over and through the catalyst in a trickle phase under a mixture of carbon monoxide and hydrogen at the selected conditions of temperature and pressure. It will, of course, be recognized that the illustrated reactants and solvents are capable of undergoing other reactions besides the desired primary one, and that, depending upon the particular conditions and specific catalyst and solvent chosen, there will be concomitant production of other products in variable amounts, most particularly methanol. It is of course desired that reaction conditions in the instant process be preferably regulated so as to produce high selectivity to the desired glycol aldehyde. Typical hydroformylation temperatures of about 50° to 200° C., most preferably about 100° C. to 130° C., are employed, together with superatmospheric pressures ranging from about 500 to 10,000 psia, most preferably about 3,000 to 5,000 psia; lower or higher pressures and temperatures can be employed if so desired. For best results residence times of the order of one to four hours are maintained in the reaction zone.

While carbon monoxide and hydrogen react in a stoichiometric one-to-one ratio, it is not necessary to have the reactants present in such proportion in order to undertake the reaction. As indicated above, the reactants should be employed in significant amounts so as to provide a desirable reaction rate. The carbon monoxide and hydrogen reactants may conveniently be supplied from synthesis gas and the like; however, they can also be present in widely varying and variable ranges, including having molar ratios from about 5 to 95, to 95 to 5. Excellent yields can be obtained when operating with carbon monoxide to hydrogen partial pressure ratios as high as 10 to 1. Large excesses of hyrogen have a tendency to favor the production of undesirable methanol, while it is often advantageous to have at least an equimolar amount of carbon monoxide present, particularly if the temperature or other reaction conditions are such so as to present a need to suppress methanol production.

A suitable source of formaldehyde can be any one of those known in the art, including paraformaldehyde, methylal, formalin solutions, polyoxymethylenes and the like. Of these, paraformaldehyde is the preferred and maximum yields have been obtained from its use.

Since it has been discovered that the preferred class of transition metal-phosphine-amide catalysts disclosed in prior copending U.S. Application Ser. No. 508,704 have been found to be ineffective for hydrogenating glycol aldehyde to ethylene glycol, there is still a great need for the development of a process in which the reaction product glycol aldehyde can first be effectively extracted from the catalyst containing solvent phase, as well as from the other reaction products, and subsequently hydrogenated in the presence of a suitable catalyst. As disclosed, infra, the use of at least one member of a class of lipophilic phosphine-amide ligands, particularly in conjunction with a rhodium moiety, having incorporated therein an ancillary tertiary amide group permits the catalyst to function both as a particularly active catalyst in the hydroformylation of formaldehyde to glycol aldehyde while also being particularly adaptable for processing in subsequent separation techniques. These ligands are extremely soluble in non-polar organic media, in sharp contrast to the earlier preferred class of phosphine-amides disclosed in Ser. No. 508,704, and thus such catalysts are exceptionally adaptable to subsequent separation operations. The synthesis of such a class of lipophilic catalysts involves introducing a concept believed to be novel in carbonylation chemistry, that is, attaching a long "organic tail" onto the remaining polar catalyst moiety, i.e., the nitrogen, to form a lipophilic ligand, a molecule which exhibits substantial solubility in a non-polar medium even though containing a substantial polar moiety within its structure. The most preferred species of the class of phosphine amide ligands is $PPh_2CH_2CH_2C(O)N(CH_3)(C_{18}H_{37})$; (Ph=phenyl).

The necessity to efficiently extract and recycle the catalyst after formation of the glycol aldehyde product, in the substantial absence of water, has led to the development of a solvent mixture comprising a relatively low boiling, polar organic which is particularly suitable as a hydroformylation solvent, in combination with a relatively high boiling, non-polar organic fluid which is immiscible with the glycol aldehyde product; the solvent mixture further incorporating an organic separation enhancing solvent, which preferably has a substantial density difference from the glycol aldehyde precipitate, and is substantially immiscible with the glycol aldehyde precipitate, thereby permitting an easy separation of the two phases. The solvent preferably is miscible with the non-polar solvent and can also readily dissolve the catalyst, since the solvent is used to wash the glycol aldehyde precipitate and thereby assists in the recovery of catalyst residue. Most preferably, the solvent also prevents the formation of any undesired azeotrope formed by methanol and the hydroformylation solvent, thereby facilitating the separation and subsequent recycle of the hydroformylation solvent back to the hydroformylation reaction zone.

The presence of a relatively low boiling, polar organic solvent is essential in order to promote the hydroformylation reaction. The following solvents are adaptable as effective low boiling, e.g., below about 90° C., at atmospheric pressure, polar organic solvents for the process: acetonitrile, t-butyl alcohol, methyl acetate, acetone, methyl ethyl ketone, nitromethane, acetaldehyde, hexafluoroacetone and the like, as well as mixtures thereof. Acetonitrile is the preferred species.

The additional presence of a high boiling, e.g., above about 100° C., at atmospheric pressure, non-polar organic solvent which is immiscible with the glycol aldehyde phase is necessary to recover and recycle the expensive hydroformylation catalyst back to the reactor without permitting the catalyst to migrate from this phase in which it resides into glycol aldehyde, and thereby become lost. This class of solvents must also be readily and efficiently separable from the low boiling polar organic solvent by using their boiling point differences in distillation as the means for separation. Suitable solvents are m-xylene, o-xylene, p-xylene, toluene, ethylbenzene, chlorobenzene, tetrachloroethylene, methylcyclohexane, octane, decane, tetralin, decalin, 1,2,3,4-tetramethylbenzene, 1,2,4-trimethylbenzene, 1,2,3 trimethylbenzene and the like, as well as mixtures thereof, with the xylenes the preferred species.

The presence of a suitable separation enhancing co-solvent is essential for the effective recovery of the expensive catalyst. Suitable solvents can be found in the class of aliphatic hydrocarbons and aliphatic ethers, e.g., pentane, hexane, heptane, diethyl ether, ethyl propyl ether, dipropyl ether and the like, as well as mixtures thereof. The preferred species will be determined by the choice of hydroformylation and polar organic solvent. The most preferred solvent mixture is a 10–90 wt. % xylene, 10–90 wt. % acetonitrile and 2–10 wt. % diethyl ether mixture.

Returning to FIG. 1, the effluent from the reaction zone 10 will typically comprise product glycol aldehyde, coproduct methanol, unreacted formaldehyde polymer, along with the solvent mixture, i.e., xylene, acetonitrile and diethyl ether, with the rhodium catalyst present in the xylene layer. This stream exits hydroformylation zone 10 at a temperature of about 100° to 130° C. and passes through line 24 into first distillation zone 26 where the hydroformylation and separation enhancing solvents are separated through a series of fractional distillations under a suitable vacuum. It will, of course, be understood that distillation zone 26, as well as all of the remaining zones illustrated in the process, can comprise one or more units of any particular type known to those skilled in the art, and in which the necessary process conditions required for efficient operation are capable of existing. Typically, the mixture is first distilled within a temperature range of about 30° to 75° C. under a vacuum of about 50 to 350 mm Hg to separate the acetonitrile, along with the diethyl ether and the major byproduct, methanol, from the reaction mixture. The distillation is carried out in the presence of a sufficient amount of CO, so as to stabilize the lipophilic catalyst, i.e., the rhodium phosphine amide, from decomposing. The xylene, formaldehyde polymer, glycol aldehyde and hydroformylation catalyst mixture pass from first distillation zone 26 through line 28 at a temperature of about 50° to 90° C. and pass into separation zone 30 for further processing. The distilled acetonitrile, methanol and diethyl ether exit zone 26 at a temperature of about 30° to 60° C. and pass through line 32 into second distillation zone 34, in which the acetonitrile is separated under elevated pressure and exits the zone through line 36. Second distillation zone is preferably kept at a temperature of about 70° to 150° C., and pressures of 15 to 100 psia; the distilled ether-methanol mixture pass from zone 34 through line 38 into the third distillation zone 40, which is preferably kept in a temperature range from about 70° to 130° C. and a pressure of 30 to 90 psia. In distillation zone 40 methanol is separated as a byproduct of the process through line 42, while the ether passes through line 44 and preferably goes to extraction zone 45. In extraction zone 45, which is preferably kept at a temperature of 20° to 50° C., the ether contacts, preferably as a countercurrent stream, with the glycol aldehyde-formaldehyde polymer precipitate, and substantially removes the remaining amount of entrained xylene, which also contains a significant amount of expensive catalyst, from the precipitate. The glycol aldehyde-formaldehyde polymer precipitates out of the immiscible xylene phase in separation zone 30; however, a complete separation is difficult since the difference in density of the two phases is not substantial. The density of diethyl ether, and the class of operable organic cosolvents, is substantially different from the glycol aldehyde precipitate, however, and, the preferred ether can also easily and selectively dissolve the expensive catalyst together with xylene, thereby making a complete, effective and economical separation of the catalyst, solvent and product possible. The glycol aldehyde and formaldehyde precipitates are collected and removed from the extraction zone 45 through line 46 and passed to fourth distillation zone 48. The xylene solvent phase, containing substantially all of the rhodium catalyst except for a small residual amount entrained on the glycol aldehyde precipitate, is recycled through line 29 back to reaction zone 10. Stream 29 can also be recharged with fresh solvent and/or catalyst before or while entering reaction zone 10.

Ether stream 44 in the extraction zone 45 functions as a washing agent to substantially remove the residual remaining xylene particles entrained in the glycol aldehyde. Since there is a small density difference between xylene and glycol aldehyde, an emulsion between the two phases has a tendency to form, further hampering a complete phase separation, and the glycol aldehyde often becomes entrained by the residual xylene present which contains the catalyst. The entrapped xylene and catalyst are nearly completely recovered by contacting and being washed by ether stream 44. The ether is then recycled through line 18 back to reaction zone 10.

It is desired to separate the unreacted formaldehyde polymer from the glycol aldehyde before hydrogenation since formaldehyde reacts with $H_2$ to make undesired methanol. Since glycol aldehyde is unstable at elevated temperatures, it is necessary to distill the mixture at temperatures below 120° C., but at least above 70° C. since this is the minimum temperature required to decompose the formaldehyde polymer so it can be vaporized during distillation. In order to avoid the extremely low vacuum required to maintain the temperature below 120° C. at the distillation column bottom, acetonitrile or another low boiling solvent is supplied through line 50, preferably comprising part of line 36 exiting the second distillation zone, to bring the pressure up to about 50–300 mm Hg. The resulting overhead condensate stream, comprising non-polymeric formaldehyde and acetonitrile, passes through line 22, preferably merging with acetonitrile recycle line 36 on the way and is recycled back to the hydroformylation reaction zone 10. It is preferred to add fresh acetonitrile solvent to either or both of these streams while recycling. The vacuum distillation zone bottoms containing glycol aldehyde, acetonitrile, and a small amount of unremoved formaldehyde polymer passes from zone 48 through line 52 and enters stripping zone 54, in which the acetonitrile solvent is stripped from the glycol aldehyde stream by contacting with a carbon monoxide gas stream 56, which enters stripping zone 54 at a temperature of about 20° to 120° C. Upon completion of contacting the CO-acetonitrile mixture exits through line 20 at a temperature of about 20° to 120° C. and, in like manner as line 22, is recycled to the hydroformylation reaction zone. In order to maintain glycol aldehyde, which is now free of acetonitrile, in its liquid state, (melting point of 97° C.) it is preferred to contact and dissolve the glycol aldehyde in a suitable polar organic solvent, preferably ethylene glycol, which enters separation zone 54 through line 58 and contacts and dissolves the glycol aldehyde, which then passes from the zone through line 60, and enters hydrogenation zone 62.

Reference numeral 62 represents a hydrogenation zone, which preferably comprises one or more reactors of any particular type known to those skilled in the art and which insures satisfactory contact between the substrate, catalyst and hydrogen. The hydrogen stream 64 is preferably employed in a substantially pure form such as is available commercially, but inert diluents such as carbon dioxide, nitrogen, methane and the like can be tolerated. The presence of such inert diluents does not affect the hydrogenation reaction but their presence makes it necessary to increase the total pressure in order to maintain the desired hydrogen partial pressure. Upon entering the hydrogenation unit, the glycol aldehyde, ethylene glycol solvent, and hydrogen are contacted in the presence of a suitable hydrogenation catalyst, or mixture of catalysts which are well known to those in the art. The preferred catalysts can be either homogeneous catalysts such as those disclosed in U.S. Pat. Nos. 4,317,946 or 4,321,414; alternatively, the catalysts can be heterogeneous catalysts such as ruthenium or carbon described by Rylander, "Catalytic Hydrogenation on Organic Synthesis", p. 73, Academic Press, N.Y., N.Y.

The hydrogenation process may be carried out, depending upon catalyst concentration, using hydrogen pressures as low as 10 to 500 psia and at temperatures ranging from 20° to 300° C. Higher pressures and temperatures may be used if so desired, but usually it is unnecessary to employ pressures much above 500 to 1,000 psia or temperatures substantially higher than 200° to 300° C., as long as an industrially acceptable rate of reaction is maintained. The hydrogenation catalyst used is preferably recovered after the hydrogenation is completed and either used again or readily reactivated if so desired by procedures known to those skilled in the art. For best results, residence times of the order of 10 to 150 minutes are maintained. Although the hydrogenation reaction will theoretically consume 1 molar part of hydrogen per part flycol aldehyde, it is desired that an excess of hydrogen be present, e.g., about 50 to 2,000% excess of hydrogen is preferred. Upon completion of the hydrogenation, the effluent product from hydrogenation zone 62 will typically comprise ethylene glycol together with any unreacted glycol aldehyde, hydrogen, ethylamine byproduct and some accompanying catalyst. This stream leaves the hydrogenation zone through line 66 and is readily separated in conventional manner in fifth distillation zone 68 into stream 72, comprising the more volatile compounds such as hydrogen and ethylamine, and stream 70, primarily comprising the ethylene glycol product. It is preferred to divert a portion of this stream back to stripping zone 54 as a solvent to dissolve glycol aldehyde. The remainder is taken off and may be further purified, if so desired, by conventional refining techniques. Ethylene glycol of high purity can be obtained through such an operation.

As in other processes of this kind, the process scheme can be contacted in either a batch, semi-continuous or continuous mode of operation; the continuous as so outlined is preferred, particularly for industrial scale operations. It is also naturally desirable to construct the various units from materials which can withstand the operating temperatures and pressures required while keeping the internal surfaces of the reactor substantially inert. Standard equipment known to permit control of the reaction, such as heat exchangers and the like may be used.

The reaction resulting in the production of ethylene glycol form the hydroformylation of formaldehyde, hydrogen and carbon monoxide is usually substantially complete within a period of about 1 to 10 hours, although reaction time is not a critical parameter of the process and longer or shorter times may be effectively employed.

The amount of rhodium-phosphine-amide catalyst employed in the hydroformylation reaction process has not been found to be critical and can, in fact, vary considerably. At least a catalytically effective amount of catalyst should be present, and preferably a sufficient amount of catalyst which is effective to provide a reasonable reaction rate.

The following examples are provided to illustrate the invention in accordance with the principles described herein but are not construed as limiting the invention in any manner except as indicated by the appended claims.

EXAMPLE 1

In a continuously run pilot plant, 387 gr/hr of formaldehyde (line 12), 21.2 gr/hr or hydrogen (14), 868 gr/hr of CO (16), together with four recycled streams (18, 20, 22, 29) containing 219 gr/hr of formaldehyde; 537 gr/hr of diethyl ether, 4,310 gr/hr of acetonitrile, 1,675 gr/hr of toluene and 58 gr of lipophilic rhodium-phosphine-amide catalyst are added to an autoclave reactor of 35 liters in volume. The hydroformylation reactor is maintained at a temperature of 110° C. and a pressure of 3800 psia. The effluent from the reactor, after its pressure is reduced to near atmosphere level to enable the release of uncondensible gas present, is passed into a 30 tray first distillation column (26). The feed stream comprising the reactor effluent contains 230 gr/hr formaldehyde, 535 gr/hr diethyl ether, 4,240 gr/hr acetonitrile, 690 gr/hr glycol aldehyde, 1,672 gr/hr toluene, 27 gr/hr methanol, and 58 gr/hr catalyst. In addition, a CO gas stream at a rate of 84 gr/hr is bubbled into the column bottom. The column is maintained at a bottoms temperature of 70° C. and a pressure of 350 mm Hg. Essentially all acetonitrile, methanol and diethyl ether along with some formaldehyde and toluene are distilled to the overhead of the column. The distillate (32) is sent to a second distillation column which consists of 40 trays and is maintained at a bottoms temperature of 136° C. and a pressure of 65 psia. In the column 530 gr/hr of ether and 24 gr/hr of methanol byproduct are taken overhead as the distillate and pass to a third distillation column, which contains 30 trays, to separate the ether and methanol. The third column is maintained at a bottoms temperature of 110° C. and a pressure of 68 psia. The liquid removed from the bottom of the column at a rate of 27 gr/hr contains 80% methanol, with the balance being formaldehyde and diethyl ether. The distillate removed at the overhead at a rate of 530 gr/hr contains 98% diethyl ether, the balance comprising methanol and formaldehyde. This distillate is next used as the washing liquid in the extractor, to be discussed later. The bottoms of the first distillation column, containing 1,283 gr/hr toluene, 690 gr/hr glycol aldehyde, 210 gr/hr formaldehyde polymer, and 58 gr/hr of catalyst, pass into a separator (30). In the separator, maintained at a temperature of 30° C., the glycol aldehyde and formaldehyde polymers precipitate out of the immiscible toluene phase. The phase separation, however, is not complete. Because of the small density difference between toluene and glycol aldehyde, and emulsion between the two phases forms. The toluene phase containing the dissolved catalyst and also a small amount of entrained glycol aldehyde, is recycled back (line 29) to the hydroformylation reactor. The glycol aldehyde and formaldehyde polymer phase together with the entrained toluene containing catalyst is sent to an extractor, in which, at 40° C. and atmospheric pressure, it is countercurrently washed by the diethyl ether stream distillated (line 44) from the third distillation column. The ether, which is immiscible with glycol aldehyde and the formaldehyde polymers, dissolves the entrained toluene and catalyst and removes them from the former phase. The ether phase (18) leaving the overhead of the extractor is then recycled back to the hydroformylation reactor. The 683 gr/hr of glycol aldehyde and 210 gr/hr of formaldehyde (46) leaving the bottom of the extractor are sent to the fourth distillation column. The vacuum column which consists of 20 trays is maintained at a bottoms temperature of 110° C. and a bottoms pressure of 200 mm Hg by feeding 477 gr/hr of the second distillation column bottoms which contains 90% acetonitrile and 10% toluene to the bottoms of the column. In the vacuum column, the formaldehyde polymers decompose into formaldehyde monomers which are sent as the distillate at a rate of 200 gr/hr along with 390 gr/hr of acetonitrile and 20 gr/hr toluene to the hydroformylator. The distillate is combined with the removal of the bottoms of the second distillation column and recycled back to the hydroformylation reactor The bottoms of the vacuum column, which contains 676 gr/hr glycol aldehyde, 40 gr/hr acetonitrile and 28 gr/hr toluene, is combined with 620 gr/hr of ethylene glycol which has been diverted from the bottoms of the fifth distillation unit (68). The combined stream is passed to the top of a 20 tray stripping column. Carbon monoxide at a rate of 140 gr/hr is fed to the bottom of the column and strips out acetonitrile and toluene from the liquid feed. The column is maintained at a bottoms temperature of 60° C. and pressure of 350 mm Hg. The bottoms of the column, which is esentially free of acetonitrile and toluene, is then fed to a trickle bed reactor of 1" in diameter and 12 ft. in length. The reactor is packed with a ruthenium on carbon catalyst and maintained at a temperature of 160° C. and a pressure of 500 psia. Hydrogen is fed in at a rate of 40 gr/hr to the reactor. Essentially all the glycol aldehyde is converted to ethylene glycol in the reactor. The exit stream 66 from the reactor contains 1,280 gr/hr of ethylene glycol, along with trace amounts of lighter compounds such as ethylamine which is created by the hydrogenation of the acetonitrile retained in the glycol aldehyde feed. The reactor effluent is sent to the fifth distillation column in order to distill out the trace amounts of lighter compounds from the ethylene glycol product. The 20 tray column is maintained at a bottoms temperature of 172° C. and a pressure of 386 mm Hg. A portion of the ethylene glycol product from the column bottom is sent back to the acetonitrile stripper to dissolve the aldehyde-glycol fed to the stripper. The remaining net 662 gm/hr of ethylene glycol is product.

EXAMPLE 2

A 300 cc stainless steel autoclave equipped with a stirrer, thermocouple, and cooling coil was charged with 65 gr acetonitrile, 30 gr m-xylene, 5 gr diethyl ether, 9.0 gr of 95% paraformaldehyde (285 mmole of equivalent formaldehyde), 0.121 dicarbonylacetylacetonato rhodium(I) (0.469 mmole), 0.055 gr trifluoroacetic acid (0.482 mmole), and 0.728 gr N-methyl-N-octadecyl-3-diphenylphosphinopropionamide (1.39 mmole) which had been sparged with dry nitrogen. The autoclave was sealed and the air was further removed by flushing the autoclave three times with carbon monoxide at 100 psi. The autoclave was then charged with 1750 psi carbon monoxide and 450 psi hydrogen at room temperature. A 2-liter autoclave reservoir was also charged with these same gas pressures and heated to 270° C. to a total pressure of 3900 psi. The reactor autoclave was heated to 110° C. for 3.0 hours to a total pressure of 3800 psi. When gas uptake lowered the pressure to 3600 psi, gas was transferred from the reservoir autoclave to the reactor autoclave during the run. Analysis of the liquid products by gas chromotography and high pressure liquid chromotography revealed 104 mmole formaldehyde remaining (64% conversion), 165 mmole glycol aldehyde and 4 mmole ethylene glycol (93% selectivity), 6 mmole glyceraldehyde (3% selectivity), and 6 mmole methanol (3% selectivity).

The glycol products and remaining formaldehyde were separated from the rhodium catalyst by first distilling the volatiles (acetonitrile, diethyl ether, trifluoroacetic acid) with a 5 plate ⅜" diameter Oldershaw column at a 1:1 reflux ratio with 180 mm Hg pressure under a carbon monoxide sparge at 45°-60° C. The glycol aldehyde and remaining formaldehyde precipitated into a separate oily layer when the volatiles were removed. The orange rhodium catalyst remained in the m-xylene layer which was decanted. The last traces of m-xylene in the glycol aldehyde were washed with 5 gr of diethyl ether which was separated from the other volatiles in a subsequent step. The similar densities of m-xylene and glycol aldehyde makes this necessary. Rhodium analysis of the glycol aldehyde layer showed 86 ppm Rh. The excess formaldehyde was distilled to give pure glycol aldehyde.

First Recycle

The combined m-xylene and diethyl ether with the soluble rhodium catalyst from the first cycle were again combined with 9.0 gr 95% paraformaldehyde, 0.055 gr (0.482 mmole) trifluoroacetic acid, 65 gr acetonitrile, charged into the autoclave, and reacted at 110° C. for 3.0 hours as before. Analysis of the liquid products revealed 140 mmole of formaldehyde remaining (51% conversion) with 142 mmole of glycol aldehyde and 2 mmole of ethylene glycol (99% selectivity), and 1 mmole of methanol (1% selectivity). The volatile acetonitrile and diethyl ether were distilled off as before to precipitate the glycol aldehyde and remaining formaldehyde. The rhodium catalyst remained in the m-xylene layer. The glycol aldehyde layer was washed with diethyl ether as before and the ether was combined with the m-xylene. Atomic absorption indicated 95 ppm rhodium in the glycol aldehyde layer.

Second Cycle

The recycled m-xylene and diethyl ether with the soluble rhodium catalyst were again combined with 9.0 gr 95% paraformaldehyde (285 mmole), 0.055 gr trifluoroacetic acid (0.482 mmole), 65 gr acetonitrile and reacted in the same way as before. Analysis of a liquid sample indicated 131 mmole of formaldehyde remaining (54% conversion) with 145 mmole of glycol aldehyde and 2.8 mmole of ethylene glycol (96% selectivity), and 3.1 mmole of methanol (20% selectivity). The volatiles were distilled in the same way precipitating glycol aldehyde which was washed with purified diethyl ether as before to wash out the last remaining rhodium entrained in the glycol aldehyde. Analysis of the glycol aldehyde layer by atomic absorption indicated 34 ppm rhodium.

Third Cycle

The m-xylene-diethyl ether solvent mixture with the rhodium catalyst was again combined with 0.054 gr trifluoroacetic acid (0.474 mmoles), 9.0 gr 95% paraformaldehyde (285 mmole equivalent formaldehyde), 65 gr acetonitrile and charged into the autoclave at the above conditions. Analysis of the liquid products revealed 154 mmole of formaldehyde remaining (46% conversion), 127 mmole of glycol aldehyde and 2.3 mmole of ethylene glycol (99% selectivity) and no detectable methanol. Analysis of the glycol aldehyde layer by atomic absorption after catalyst separation as above indicated 64 ppm rhodium.

Fourth Recycle

The recovered rhodium catalyst in the m-xylene diethyl ether solvent mixture was again combined with 0.055 trifluoroacetic acid (0.482 mmole), 9.0 gr 95% paraformaldehyde, (285 mmole), 65 gr acetonitrile and charged into the autoclave under the above conditions. Analysis of the liquid products after reaction revealed 170 mmole of formaldehyde remaining (40% conversion), 101 mmole of glycol aldehyde (88% selectivity) and no detectable methanol. The glycol aldehyde was separated from the rhodium catalyst as before and 96 ppm rhodium was measured in the glycol aldehyde by atomic absorption. In principle the catalyst could be recycled many more times in the same manner.

COMPARATIVE EXAMPLE

The 300 cc stainless steel autoclave was charged with 65 gr acetonitrile, 30 gr m-xylene, 5 gr diethyl ether, 9.0 gr 95% paraformaldehyde (285 mmole of equivalent formaldehyde), 0.121 gr dicarbonylacetylacetonato rhodium (I) (0.469 mmole), 0.054 gr trifluoroacetic acid (0.474 mmole), and 0.397 gr N,N-dimethyl-3-diphenylphosphinopropionamide (1.39 mmole) which had been sparged with dry nitrogen. The autoclave was sealed and the reaction was carried out under identical conditions to Example 2. Analysis of the liquid products by gas chromatography and high pressure liquid chromatography revealed 59 mmole of formaldehyde (79% conversion), 185 mmole of glycol aldehyde and 2 mmole of ethylene glycol (83% selectivity), 8 mmole of glyceraldehyde (4% selectivity), and 8 mmole of methanol (4% selectivity).

The glycol products and formaldehyde were separated from the rhodium catalyst by first distilling the volatiles with a 5 plate ⅜" diameter Oldershaw column at a 1:1 reflux ratio with 180 mm Hg pressure under a carbon monoxide sparage at 45°-60° C. The glycol aldehyde and remaining formaldehyde precipitated when the volatiles were removed. Both the m-xylene and the oily layer of glycol aldehyde and unreacted formaldehyde were red in color. Determination of rhodium in the glycol aldehyde layer revealed 2100 ppm rhodium by atomic absorption.

First Recycle

The m-xylene solution rhodium catalyst was combined with 5 gr diethyl ether, 65 gr acetonitrile, and 9.0 gr 95% paraformaldehyde (285 mmole equivalent formaldehyde) and charged into the 300 cc autoclave as before. It was reacted under identical conditions to the first cycle. After cooling, the analysis of the liquid products revealed 182 mmole formaldehyde left (36% conversion) with 70 mmole of glycol aldehyde (68% selectivity) and 20 mmole methanol (19% selectivity). Only 180 ppm Rh (measured by atomic absorption) was still in the liquid solution.

Other rhodium catalyst precursors could be recycled in a similar manner with the lipophilic phosphine cocatalyst.

EXAMPLE 3

The 300 cc stainless steel autoclave was charged with 65 gr acetonitrile, 30 gr m-xylene, 5 gr diethyl ether, 9.0 gr 95% paraformaldehyde (285 mmole of equivalent formaldehyde), 0.092 gr chlorodicarbonylrhodium (I) dimer (0.24 mmole) and 0.737 gr N-methyl-N-octadecyl-3-diphenyl phosphinopropionamide (1.41 mmole) which had been sparged with dry nitrogen. The autoclave was sealed and flushed three times with carbon monoxide at 100 psi. The autoclave was then charged with 1750 psi carbon monoxide and 450 psi hydrogen at room temperature. The reactor autoclave was heated to 120° C. for 3.0 hours to a total pressure of 3600 psi. When gas uptake lowered the pressure to 3300 psi, gas was transferred from a reservoir autoclave to the reactor autoclave. After the reactor was cooled and vented, analyses of the liquid products by gas and high pressure liquid chromotography revealed 58 mmole of formaldehyde (80% conversion), 152 mmole of glycol aldehyde and 4 mmole of ethylene glycol (69% selectivity), 18 mmole of glyceraldehyde (8% selectivity), and 31 mmole of methanol (14% selectivity).

The glycol products and remaining formaldehyde were separated from the rhodium catalyst by first distilling the volatiles (acetonitrile, diethyl ether, trifluoroacetic acid, methanol). The glyceraldehyde, glycol aldehyde and remaining formaldehyde separated into a separate oily phase when the volatiles had been removed. The m-xylene solution in which the rhodium catalyst was dissolved was decanted. Atomic absorption of the glycol aldehyde mixture revealed 24 ppm rhodium.

First Recycle

The m-xylene solvent mixture with the rhodium catalyst from the first cycle was combined with 9.0 gr 95% paraformaldehyde (285 mmoles), 5 gr diethyl ether, 65 gr acetonitrile, and reacted at 120° C. for 3.0 hours as before.

After cooling and venting, analysis of the liquid products revealed 116 mmole formaldehyde remaining (59% conversion), 122 mmole glycol aldehyde and 2 mmole ethylene glycol (73% selectivity), 10 mmole glyceraldehyde (6% selectivity), and 15 mmole methanol (9% selectivity). The volatiles were removed to separate the m-xylene layer containing the soluble rhodium catalyst from the organic reactants and products. Atomic absorption of the glycol aldehyde revealed 12 ppm rhodium.

Second Recycle

The m-xylene with the rhodium catalyst was combined with 5 gr diethyl ether, 65 gr acetonitrile, and 9.0 gr paraformaldehyde (285 mmole formaldehyde). The mixture was purged with nitrogen, charged into the autoclave in Example 1, are reacted at 120° C. for 3.0 hours under the same carbon monoxide-hydrogen pressures as before. The vessel was cooled, vented, and the volatiles removed as before. Analysis of the liquid phase revelaed 122 mmole of formaldehyde remaining (57% conversion) with 107 mmole glycol aldehyde and 1 mmole ethylene glycol (66% selectivity), 5 mmole glyceraldehyde (3% selectivity), and 4 mmole methanol (2% selectivity). Atomic absorption of the glycol aldehyde layer revealed 66 ppm rhodium. The remainder was in the m-xylene phase as before.

Third Recycle

The m-xylene with the rhodium catalyst was combined with 5 gr diethyl ether, 65 gr acetonitrile, and 9.0 gr paraformaldehyde (285 mmole). It was again charged into the same autoclave and reacted at 120° C. under the same pressure of carbon monoxide-hydrogen for 3.0 hours. Analysis of the liquid products revealed 140 mmole for formaldehyde remaining (51% conversion), 84 mmole of glycol aldehyde (58% selectivity), 1 mmole of glyceraldehyde (1% selectivity), and 1 mmole of methanol (1% selectivity).

In principle, the same technique could be used to recycle the rhodium catalyst many times.

EXAMPLE 4

Separation of Formaldehyde and Glycol Aldehyde

After the glycol aldehyde product and remaining unreacted formaldehyde were separated from the rhodium catalyst, 8.5 gr of the mixture which contained approximately 65% glycol aldehyde and 35% polymeric formaldehyde were added to 39.5 gr of acetonitrile. The resulting solution was distilled at atmospheric pressure with a carbon monoxide sparge. The overhead temperature was 83° C. and the pot temperature ranged between 90°–110° C. The formaldehyde comprised 95%, and the glycol aldehyde 4%, of the overhead. The final bottoms mixture after distillation contained 88% glycol aldehyde and 7% formaldehyde.

We claim:

1. A process for the preparation of ethylene glycol through a glycol aldehyde intermediate comprising:
   (A) reacting formaldehyde, hydrogen and carbon monoxide in a hydroformylation reaction zone to form glycol aldehyde in the presence of an effective solvent mixture comprising:
   (1) a low boiling, polar, organic, hydroformylation solvent,
   (2) a high boiling, non-polar organic solvent,
   (3) a low boiling organic separation enhancing solvent;
   the reaction proceeding in the presence of a lipophilic catalyst selected from a class of phosphine-amide ligands in conjunction with an effective transition metal;
   (B) separating the hydroformylation solvent and the separation enhancing solvent from the hydroformylation zone effluent;
   (C) separating the glycol aldehyde-unreacted formaldehyde phase from the remaining reaction zone effluent, now comprising the high boiling, non-polar organic solvent containing the lipophilic catalyst;

(D) contacting and washing the separated glycol aldehyde-formaldehyde phase with the separation enhancing solvent in an extraction zone to substantially extract the remaining high boiling, non-polar organic as well as any catalyst contained therein;

(E) recycling the separation enhancing solvent and the high boiling, non-polar organic solvent containing substantially all the lipophilic catalyst to the hydroformylation zone;

(F) separating the glycol aldehyde from the formaldehyde;

(G) hydrogenating the glycol aldehyde in a hydrogenation zone to ethylene glycol;

(H) separating ethylene glycol from the hydrogenation zone effluent.

2. A process as claimed in claim 1 wherein the preparation of glycol aldehyde in a hydroformylation zone occurs under effective superatmospheric pressure and elevated temperature conditions.

3. A process as claimed in claim 1 wherein the hydroformylation solvent is selected from acetonitrile, t-butyl alcohol, methyl acetate, acetone, methyl ethyl ketone, nitromethane, acetaldehyde, hexafluoroacetone and various mixtures thereof.

4. A process as claimed in claim 3 where the hydroformylation solvent is acetonitrile.

5. A process as claimed in claim 1 wherein the high boiling non-polar organic solvent is selected from xylene, toluene, ethylbenzene, chlorobenzene, tetrachloroethylene, methylcyclohexane, octane, decane, tetralin, decalin and various mixtures thereof.

6. A process as claimed in claim 5 wherein the high boiling non-polar organic solvent is xylene.

7. A process as claimed in claim 1 wherein the separation enhancing organic solvent has a substantial density difference from the glycol aldehyde-formaldehyde phase and is substantially immiscible to glycol aldehyde.

8. A process as claimed in claim 7 wherein the separation enhancing solvent is substantially miscible to the high boiling, non-polar organic solvent and also can dissolve the lipophilic catalyst.

9. A process as claimed in claim 8 wherein the solvent is also capable of breaking an azeotrope formed by methanol and the hydroformylation solvent.

10. A process as claimed in claim 1 wherein the separation enhancing solvent is selected from pentane, hexane, heptane, diethyl ether, ethyl propyl ether, dipropyl ether and various mixtures thereof.

11. A process as claimed in claim 10 wherein the separation enhancing solvent is diethyl ether.

12. A process as claimed in claim 1 wherein the solvent mixture is a 10–90 wt. % xylene, 10–90 wt. % acetonitrile and 2–10 wt. % diethyl ether mixture.

13. A process as claimed in claim 1 wherein the lipophilic catalyst is $RhPPh_2CH_2CH_2CH_2C(O)N(CH_3)[(CH_2)_{17}CH_3]$.

14. A process as claimed in claim 1 wherein the separation of the hydroformylation and separation enhancing organic solvent from the remaining hydroformylation zone effluent is by distillation.

15. A process in claim 14 wherein the distillation occurs at a temperature of about 30°–75° C. and a pressure of about 150–350 mm Hg, in the presence of an effective amount of CO to stabilize the lipophilic catalyst.

16. A process as claimed in claim 14 wherein the hydroformylation and separation enhancing organic solvents are separated by a second distillation.

17. A process as claimed in claim 16 wherein the separation enhancing organic solvent is further separated from any methanol byproduct present and passed to an extraction zone.

18. A process as claimed in claim 16 wherein the separated hydroformylation solvent is partially recycled to the hydroformylation zone and partially passed to a zone where it is distilled and contacted with the glycol aldehyde-formaldehyde phase.

19. A process as claimed in claim 1 wherein the glycol aldehyde-formaldehyde phase is precipitated from the remaining hydroformylation zone effluent in a separation zone.

20. A process as claimed in claim 1 wherein only about 100 ppm of lipophilic catalyst is not recycled to the hydroformylation zone during product separation.

21. A process as claimed in claim 19 wherein the high boiling non-polar organic solvent is recycled to the hydroformylation zone from the separation zone.

22. A process as claimed in claim 18 wherein the glycol aldehyde-formaldehyde phase is separated by dissolving in the hydroformylation solvent, with the resulting glycol aldehyde-hydroformylation solvent mixture passing to a stripping zone.

23. A process as claimed in claim 22 wherein a formaldehyde-hydroformylation solvent mixture is recycled to the hydroformylation zone.

24. A process as claimed in claim 22 wherein the glycol aldehyde-hydroformylation solvent mixture is stripped with a CO gas stream and separates the glycol aldehyde from the hydroformylation solvent.

25. A process as claimed in claim 24 wherein the glycol aldehyde is dissolved in an effective polar organic and passed to a hydrogenation zone.

26. A process as claimed in claim 25 wherein the polar organic is an ethylene glycol stream.

* * * * *